(12) United States Patent
Buchman et al.

(10) Patent No.: US 9,055,765 B2
(45) Date of Patent: Jun. 16, 2015

(54) DIETARY COMPOSITIONS AND RELATED METHODS OF USE

(75) Inventors: Alan Lewis Buchman, Northfield, IL (US); Meenakshi Rammohan, Woodridge, IL (US); Amelita Reyes, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 747 days.

(21) Appl. No.: 12/358,041

(22) Filed: Jan. 22, 2009

(65) Prior Publication Data

US 2009/0215721 A1    Aug. 27, 2009

Related U.S. Application Data

(60) Provisional application No. 61/023,748, filed on Jan. 25, 2008.

(51) Int. Cl.
| | | |
|---|---|---|
| A23L 1/0524 | (2006.01) | |
| A23L 1/0562 | (2006.01) | |
| A23L 1/308 | (2006.01) | |
| A23L 2/38 | (2006.01) | |
| A23L 2/52 | (2006.01) | |
| A23L 2/60 | (2006.01) | |

(52) U.S. Cl.
CPC .............. *A23L 1/308* (2013.01); *A23L 1/0524* (2013.01); *A23L 1/05625* (2013.01); *A23L 2/38* (2013.01); *A23L 2/52* (2013.01); *A23L 2/60* (2013.01)

(58) Field of Classification Search
CPC .... A23L 1/0524; A23L 1/05625; A23L 1/308
See application file for complete search history.

(56) References Cited

U.S. PATENT DOCUMENTS

| | | | |
|---|---|---|---|
| 2,369,846 A * | 2/1945 | Olsen et al. .................... | 426/577 |
| 3,930,057 A * | 12/1975 | Jokay .............................. | 426/577 |
| 4,140,807 A * | 2/1979 | Braverman .................... | 426/573 |
| 6,458,395 B1 * | 10/2002 | Emoto ............................. | 426/72 |
| 6,541,047 B1 | 4/2003 | Claycamp | |
| 6,572,898 B2 * | 6/2003 | Nelson et al. ................. | 424/663 |
| 6,770,305 B2 | 8/2004 | Nelson | |
| 7,338,679 B2 * | 3/2008 | Uchida et al. ................. | 426/577 |
| 2005/0095271 A1 | 5/2005 | Mathewson | |
| 2005/0260322 A1 | 11/2005 | Takaichi | |

FOREIGN PATENT DOCUMENTS

JP         07118162      5/1995

OTHER PUBLICATIONS

Definition of prevent, Oxford English Dictionary, http://dictionary.oed.com, accessed online on May 27, 2010.*
Nutrition facts, Cera Products web site, http://www.ceraproductsinc.com, accessed online on Apr. 18, 2010.*
Kar et al., Carbohydrate Polymers, 1999, 40, p. 277-284.*
Definition of pudding , Oxford English Dictionary, http://www.oed.com/view/Entry/154127?, accessed online on Jan. 22, 2014.*
DeMars et al., Food Hydrocolloids, 2001, 15, p. 643-653.*
Rhoads, J.M., Journal of Pediatric Gastroenterology & Nutrition, 1998, 27(1), p. 114-115.*
Rutgers, R., J. Sci. Food Agric., 1958, 9, p. 61-68.*
Leroux et al., Food Hydrocolloids, 2003, 17, p. 455-462.*
Marcotte et al., Food Research International, 2001, 34, p. 695-70.*
Werch SC et al., "On the Fate of Ingested Pectin" 1941 Am J Dig Dis 8:101-105.
Nyman M et al., "Fermentation of dietary fibre components in the rat intestinal tract" 1982 Br J Nutr 47:357-366.
International Search Report and Written Opinion dated Sep. 7, 2009, PCT/US2009/031711.

\* cited by examiner

*Primary Examiner* — Jonathan S Lau
(74) *Attorney, Agent, or Firm* — Casimir Jones S.C.

(57) ABSTRACT

The present invention provides dietary compositions for mammalian consumption. In particular, the present invention provides compositions comprising pectin, a component comprising electrolytes, thickening agents, a sweetening agent, and water, and methods for making such compositions. In some embodiments, the dietary compositions are used for preventing and/or treating malabsorption dysfunction and associated disorders (e.g., short bowel syndrome, Crohn's disease). In some embodiments, the dietary compositions are used for preventing and/or treating colonic disorders (e.g., ulcerative colitis). The dietary compositions further find use in subjects with diarrhea, regardless of cause, subject suffering from gastric dumping syndrome, and obese patients or patients seeking to lose weight, as the composition delays gastric emptying (e.g., creating feeling of early satiety). In some embodiments, the dietary composition is a prebiotic food supplement.

20 Claims, No Drawings

DIETARY COMPOSITIONS AND RELATED METHODS OF USE

The present application claims priority to U.S. Provisional Patent Application Ser. No. 61/023,748, filed Jan. 25, 2008, the disclosure of which is herein incorporated by reference in its entirety.

STATEMENT REGARDING FEDERALY SPONSORED RESEARCH OR DEVELOPMENT

This invention was made with government support under grant number M01RR-000048 awarded by the National Institutes of Health. The government has certain rights in the invention.

FIELD OF THE INVENTION

The present invention provides dietary compositions for mammalian consumption. In particular, the present invention provides compositions comprising pectin, a component comprising electrolytes, thickening agents, a sweetening agent, and water, and methods for making such compositions. In some embodiments, the dietary compositions are used for preventing and/or treating malabsorption dysfunction and associated disorders (e.g., short bowel syndrome, Crohn's disease). In some embodiments, the dietary compositions are used for preventing and/or treating colonic disorders (e.g., ulcerative colitis). The dietary compositions further find use in subjects with diarrhea, regardless of cause, subject suffering from gastric dumping syndrome, and obese patients or patients seeking to lose weight, as the composition delays gastric emptying (e.g., creating feeling of early satiety). In some embodiments, the dietary composition is a prebiotic food supplement.

BACKGROUND

Malabsorption is a clinical term that encompasses defects occurring during the digestion and absorption of food nutrients by the gastrointestinal tract. The digestion or absorption of one or more types of nutrients (e.g., carbohydrates, fats, proteins) may be impaired in the digestion and/or transport across the intestinal mucosa into the systemic circulation. Malabsorption disorders encompass a number of different clinical entities that result in chronic diarrhea, abdominal distention, weight loss, dehydration, and/or failure to thrive. Clinical malabsorption can be broken down into several distinct conditions, both congenital and acquired, that affect one or more of the different steps in the intestinal hydrolysis and subsequent transport of nutrients.

While presenting symptoms, such as diarrhea and weight loss, may be common, the specific causes are usually established based on physiological evaluations. The treatment of the disease often depends on the establishment of a definitive etiology for the malabsorption. The osmotic load resulting from the inability of the intestine to absorb certain nutrient elements causes the presenting symptoms. Diarrhea is the most common symptomatic complaint. Additional symptoms include weight loss and fatigue, flatulence and abdominal distention, edema, anemia (e.g., microcytic (iron deficiency) or macrocytic (vitamin B-12 deficiency)).

Management of patients with malabsorption includes the correction of nutritional deficiencies and, when possible, the treatment of causative diseases (e.g., celiac disease, ulcerative colitis, small bowel syndrome). Nutritional support includes, for example, supplementing various minerals (e.g., calcium, magnesium, iron, and vitamins), caloric and protein replacement also is essential, use of medium-chain triglycerides as fat substitutes (e.g., they do not require micelle formation for absorption and their route of transport is portal rather than lymphatic), and parenteral nutrition.

Improved methods of preventing and/or treating malabsorption dysfunction and associated disorders (e.g., ulcerative colitis, short bowel syndrome, Crohn's disease) are needed.

SUMMARY

The present invention provides dietary compositions for mammalian consumption. In particular, the present invention provides compositions comprising pectin, a component comprising electrolytes, thickening agents, a sweetening agent, and water, and methods for making such compositions. In some embodiments, the dietary compositions are used for preventing and/or treating malabsorption dysfunction and associated disorders (e.g., short bowel syndrome, Crohn's disease). In some embodiments, the dietary compositions are used for preventing and/or treating colonic disorders (e.g., ulcerative colitis). In some embodiments, the dietary compositions are used for preventing and/or treating diarrhea, regardless of the cause (e.g., gastroenteritis caused by viral, parasitic, or bacterial agents, dysentery, cholera, botulism, Crohn's disease, poisoning, radiation sickness, lactose intolerance, dumping syndrome, etc.). In some embodiments, the dietary compositions are used for preventing and/or treating gastric dumping syndrome. In some embodiments, the dietary compositions are used to treat or prevent obesity or as a weight loss material, as the composition delays gastric emptying, and, for example, creates a feeling of early satiety. In some embodiments, the dietary composition is a prebiotic food supplement.

Pectin is a water soluble, non-cellulose fiber that is nearly completely fermented by colonic bacterial flora to the short chain fatty acids acetate, butyrate, and proprionate (see, e.g., Nyman M, et al., Br J Nutr 47:357-366, 1982). Only 10% of pectin is recovered in feces when given alone (15% when provided as part of a mixed meal) in normal volunteers and 94-97% after 24 hours in patients with ileostomies, suggesting significant colonic metabolism (see, e.g., Werch S C, et al., Am J Dig Dis 8:101-105, 1941). It is contemplated that short chain fatty acids are produced from the metabolism of pectin and utilized by mucosal cells (e.g., colonocytes) as fuel and serve to enhance fluid absorption. In addition, it is contemplated that short chain fatty acids assist in healing ulcerations and mucosal injury associated with colonic disorders (e.g., ulcerative colitis).

Pectin by itself is a course powder and is unpalatable. Experiments conducted during the course of development of embodiments for the present invention demonstrated that pectin can be mixed with the right concentration of electrolytes, sweeteners, and water in order to achieve a consistency that renders it palatable. For example, if too concentrated, pectin will stick to the roof of a subject's mouth. Accordingly, the present invention provides palatable dietary compositions comprising pectin.

Patients suffering from malabsorption develop profound diarrhea as well as malnutrition from insufficient energy absorption. Current treatments, however, fail to effectively address, for example, intestinal transit time, gastric emptying, energy absorption, and fluid absorption commonly associated with malabsorption. The present invention overcomes the limitations of malabsorption treatments through use of dietary compositions comprising, for example, pectin.

Indeed, the dietary compositions of the present invention prevent and/or treat malabsorption dysfunction and/or disorders through, for example, increasing intestinal transit time, decreasing gastric emptying, maintaining fluid balance, increasing energy absorption, and/or increasing fluid absorption.

Patients with colonic disorder such as, for example, ulcerative colitis develop diarrhea, ulcers, and open sores in the colon. Current treatments, however, fail to effectively address such issues commonly associated with colonic disorders. The present invention overcomes the limitations of colonic disorder treatments through use of dietary compositions comprising, for example, pectin. In particular, the dietary compositions of the present invention treat colonic disorders through, for example, bacterial fermentation of pectin thereby producing short chain fatty acids for healing colonic ulcerations and/or colonic mucosal injury.

Moreover, in some embodiments, the dietary compositions of the present invention are provided as prebiotic compositions comprising pectin. Prebiotics are a category of functional food, defined as, for example, non-digestible food ingredients that beneficially affect the host by selectively stimulating the growth and/or activity of one or a limited number of intestinal bacteria, and thus improve host health. Prebiotic compositions comprising pectin, however, represent an improvement over presently available prebiotics. In particular, prebiotic compositions comprising pectin increase intestinal transit time, decrease gastric emptying, maintaining fluid balance, increase energy absorption, and/or increase fluid absorption. The prebiotic compositions comprising pectin are not limited for use by a particular type of subject. Indeed, the prebiotic compositions can be used by several types of subjects including, but not limited to, subjects at risk for developing diarrhea (e.g., short and long distance runners, athletes prior to and/or during an athletic performance), and subjects requiring electrolyte and/or energy boosts (e.g., surgeons, lawyers, teachers, nurses, civil servants, etc.) (e.g., subjects requiring short term and/or long term amounts of energy).

Accordingly, in certain embodiments the present invention provides dietary compositions comprising pectin (e.g., approximately 0.1% to 10% by weight; 0.5% to 8% by weight; 1% to 6% by weight; 2% to 5% by weight; 2% to 4% by weight), a thickening agent (e.g., approximately 0.1% to 10% by weight; 0.5% to 8% by weight; 1% to 6% by weight; 2% to 5% by weight; 2% to 4% by weight), a component comprising electrolytes (e.g., approximately 0.1% to 10% by weight; 0.5% to 8% by weight; 1% to 6% by weight; 2% to 5% by weight; 2% to 4% by weight), and water (e.g., approximately 88 to 98% by weight; 90 to 96% by weight; 92 to 94% by weight; 93% by weight). The dietary compositions are not limited to particular preparation forms. In some embodiments, the dietary compositions are prepared as nutraceutical compositions, nutrient supplements, food products (e.g., snack foods, medical foods), or food supplements (e.g., prebiotic food supplements). In some embodiments, the dietary compositions are prepared for oral consumption by a subject (e.g., a human subject, a non-human subject). In some embodiments, the dietary compositions are configured to prevent and/or treat malabsorption dysfunction in a subject (e.g., a human subject). The dietary compositions are not limited to a particular manner for preventing and/or treating malabsorption dysfunction in a subject. In some embodiments, the dietary compositions prevent and/or treat malabsorption dysfunction through increasing intestinal transit time in the subject, decreasing gastric emptying in the subject, maintaining fluid balance, increasing intestinal energy absorption in the subject, and/or increasing intestinal fluid absorption in the subject. The dietary compositions are not limited to a particular type of component comprising electrolytes. In some embodiments, the component comprising electrolytes is CeraLyte 50, CeraLyte70, or CeraLyte90 (Cera Products, Inc.). The dietary compositions are not limited to a particular kind of thickening agent. In some embodiments, the thickening agent is gelatin or pudding mix (e.g., sugar free pudding mix). In some embodiments, the dietary compositions further comprise sweetening agents.

In certain embodiments, the present provides methods for treating a subject suffering from a malabsorption disorder comprising administering to the subject a dietary composition of the present invention. The methods are not limited to treating a particular kind of malabsorption disorder. In some embodiments, the malabsorption disorder is Crohn's disease. In some embodiments, the malabsorption disorder is short bowel syndrome. In some embodiments, the methods further comprise co-administration of the dietary compositions with an addition agent (e.g., an antibiotic, a bile acid-binding agent, a digestive enzyme, and a vitamin).

In certain embodiments, the present provides methods for treating a subject suffering from a colonic disorder and/or symptoms associated with a colonic disorder comprising administering to the subject a dietary composition of the present invention. In certain embodiments, the present provides methods for preventing development of a colonic disorder and/or symptoms associated with a colonic disorder comprising administering to a subject a dietary composition of the present invention. The methods are not limited to treating a particular kind of colonic disorder and/or associated symptom. In some embodiments, the colonic disorder is ulcerative colitis. In some embodiments, the colonic disorder includes, but is not limited to, angiodysplasia of the colon, chronic functional abdominal pain, colitis, colon cancer, constipation, Crohn's disease, diarrhea, diverticulitis, diverticulosis, irritable bowel syndrome, polyposis (e.g., colorectal polyp), ulcerative colitis, and toxic megacolon. In some embodiments, the symptoms associated with a colonic disorder include, but are not limited to, at least one of inflammation of the lining of the colon, ulcers, bleeding, diarrhea (e.g., diarrhea mixed with blood and mucus), abdominal pain, and weight loss, In some embodiments, the methods further comprise co-administration of the dietary compositions with an additional agent (e.g., 5-Aminosalicyclic acid agents (e.g., sulfasalazine, mesalamine, balsalazide), tumor necrosis factor inhibitors (e.g., infliximab), immunosuppressants (e.g., azathioprine, cyclosporine, 6-mercaptopurine), antimicrobials (e.g., ciprofloxacin, metronidazole), corticosteroids (e.g., methylprednisolone, prednisone)).

In certain embodiments, the present provides methods for maintaining normal digestive health (e.g., intestinal) and maintaining normal colonic health in a subject comprising administering to the subject a dietary composition of the present invention. In some embodiments, the dietary composition is a prebiotic composition comprising pectin.

In certain embodiments, the present invention provides methods for manufacturing the dietary compositions of the present invention. The present invention is not limited to a particular manufacturing method. In some embodiments, the method of manufacturing dietary compositions comprises, for example, combining the pectin, thickening agent and component comprising electrolytes with boiling water, and cooling the mixture.

DETAILED DESCRIPTION

Patients with malabsorption because of disease and/or insufficient small intestine may develop profound diarrhea as well as malnutrition from insufficient energy absorption. Patients with colonic disorder such as, for example, ulcerative colitis develop diarrhea, ulcers, and open sores in the colon. The present invention provides compositions and methods for preventing and/or treating malabsorption dysfunction and/or disorders (e.g., celiac disease, short bowel syndrome) and colonic disorders (e.g., ulcerative colitis), maintaining remission from such disorders, and preventing and/or reducing a need for parenteral nutrition associated with such disorders and/or treating other conditions or disorders.

The present invention is not limited to a particular composition or methods. In some embodiments, the compositions and methods act through use of an additional dietary source of energy. The compositions and methods are not limited to a particular type of additional dietary source of energy. In some embodiments, the additional dietary source of energy is a dietary composition designed for consumption (e.g., oral consumption, parenteral consumption). In some embodiments, the dietary composition is a nutraceutical composition. In some embodiments, the dietary composition is a food product. In some embodiments, the dietary composition is a food supplement (e.g., a fiber supplement). In some embodiments, the food supplement is a prebiotic food supplement. In some embodiments, the dietary composition comprises pectin.

The present invention is not limited to a particular type of palatable dietary composition comprising pectin. In some embodiments, the dietary composition (e.g., nutraceutical composition, food product, food supplement) comprises pectin in combination with specific types of components (e.g., ingredients). The dietary compositions are not limited to particular additional components (e.g., ingredients). In some embodiments, the dietary compositions comprise pectin in combination with, for example, a thickening agent, water, and/or a component comprising electrolytes.

The dietary compositions are not limited to a particular type of pectin. In some embodiments, the dietary compositions utilize pectin configured for oral and/or parenteral consumption by a mammal (e.g., human, cat, dog, cow, ape, sheep, etc.). In some embodiments, the dietary compositions comprise a citrus pectin (CP Kelco). In some embodiment, the dietary compositions comprise a modified form of pectin (e.g., high methoxy pectins such as Unipectin QC40 available from SKW Biosystems; low ester pectins such as products sold under the trade names GENU LM 22 CG and GENU LM 12 CG, partly amidated low ester pectins such as products sold under the trade names GENU LM 101 AS and GENU LM 102 AS, and amidated low ester pectins such as the product sold under the trade name GENU LM 104 AS FS, all of which pectin products are available from Hercules Ltd.). The dietary compositions are not limited to a particular amount of pectin. In some embodiments, the amount of pectin used in the dietary composition is as low as, for example, $1 \times 10^{-5}$ grams, or as high as $1 \times 10^5$ grams. In some embodiments, the amount of pectin may be from approximately 0.1% to 10% by weight based on the total weight of the dietary composition (e.g., 0.5% to 8% by weight; 1% to 6% by weight; 2% to 5% by weight; 2% to 4% by weight). In some embodiments, the amount of pectin is approximately 3% by weight based on the total weight of the dietary composition. In some embodiments, the amount of pectin used in the dietary composition is dependent upon the other components (e.g., ingredients) in the dietary composition (e.g., a thickening agent, water, and/or a component comprising electrolytes). In some embodiments, the amount of pectin used in the dietary compositions is such that it will maximize prevention and/or treatment of malabsorption dysfunction and/or colonic disorders (e.g., celiac disease, ulcerative colitis, short bowel syndrome), and/or other conditions or disorders, and prevention and/or reduction of a need for parenteral nutrition. In some embodiments, the dissolving of pectin is enhanced in dietary compositions further comprising a component comprising electrolytes.

In some embodiments, the dietary compositions comprise a thickening agent. The dietary compositions are not limited to a particular type of a thickening agent. In some embodiments, the dietary compositions utilize a thickening agent is configured for oral and/or parenteral consumption by a mammal (e.g., human, cat, dog, cow, ape, sheep, etc.). The dietary compositions are not limited to a particular type of thickening agent. In some embodiments, the thickening agent is any type of gelatin. In some embodiments, the thickening agent is a pudding mix (e.g., sugar-free pudding mix; sugar pudding mix). In some embodiments, the thickening agent is agar, alginin, arrowroot, carageenan, collagen, cornstarch, fecula, furcellaran, katakuri, rehan, roux, tapioca, guar gum, locust bean gum, xanthan gum, guar gum, gum arabic, gellan gum, locust bean gum, gum ghatti, gum tragacanth, sodium alginate, potassium alginate, propylene glycol alginate, and mixtures thereof. In some embodiments, the thickening agent may be a suitable starch including modified and unmodified starches, depending upon the desired functionality of the material, e.g., its viscosity, heat resistance, shear resistance, the amount of retorting and the like it will undergo, or any gum acceptable for use with food (e.g., xanthan gum, guar gum, gum arabic, carrageenan, gellan gum, locust bean gum, gum ghatti, gum tragacanth, agar, algin, sodium alginate, potassium alginate or propylene glycol alginate, or any mixture thereof). The dietary compositions are not limited to utilizing a particular amount of thickening agent. In some embodiments, the amount of thickening agent used in the dietary composition is as low as, for example, $1 \times 10^{-5}$ grams, or as high as $1 \times 10^5$ grams, or equivalents. In some embodiments, the amount of thickening agent used in the dietary composition is dependent upon the other components (e.g., ingredients) in the dietary composition (e.g., pectin, water, and/or a component comprising electrolytes). In some embodiments, the amount of thickening agent may be from approximately 0.1% to 10% by weight based on the total weight of the dietary composition (e.g., 0.5% to 8% by weight; 1% to 6% by weight; 2% to 5% by weight; 2% to 4% by weight). In some embodiments, the amount of thickening agent is approximately 2.5% by weight based on the total weight of the dietary composition. In some embodiments, the thickening agent is added for texture and stability. Less thickening agent results in a dietary composition that is less stable and a dietary composition with reduced yield. Too much thickening agent results in a product that is organoleptically too thick and which is difficult to process. In some embodiments, the amount of thickening agent used in the dietary compositions is such that it will maximize prevention and/or treatment of malabsorption dysfunction and/or colonic disorders (e.g., celiac disease, ulcerative colitis, short bowel syndrome), and/or other conditions or disorders, and prevention and/or reduction of a need for parenteral nutrition. In some embodiments, the thickening agent improves the taste of the dietary composition. In some embodiments, the thickening agent is used to prevent the dietary composition from developing an undesired consistency (e.g., a consistency with too much liquidity, a consistency lacking a solid form).

In some embodiments, the dietary compositions comprise a component comprising electrolytes. The dietary compositions are not limited to a particular type of component comprising electrolytes. In some embodiments, the dietary compositions utilize components comprising electrolytes configured for oral and/or parenteral consumption by a mammal (e.g., human, cat, dog, cow, ape, sheep, etc.). The dietary compositions are not limited to particular components comprising electrolytes. In some embodiments, the component comprising electrolytes is a mixture comprising varying amounts of fat, sodium, potassium, carbohydrates, sugar, natural and artificial flavors such that the mixture has an osmolarity of, for example, <250 mOsm/L (see, CeraLyte 50, Cera Products, Inc.) or <275 mOsm/L (see, CeraLyte 70, CeraLyte 90, Cera Products, Inc.). The dietary compositions are not limited to a particular amount of components comprising electrolytes. In some embodiments, the amount of components comprising electrolytes used in the dietary composition is as low as, for example, $1\times10^{-5}$ grams, or as high as $1\times10^5$ grams. In some embodiments, the amount of component comprising electrolytes may be from approximately 0.1% to 10% by weight based on the total weight of the dietary composition (e.g., 0.5% to 8% by weight; 1% to 6% by weight; 2% to 5% by weight; 2% to 4% by weight). In some embodiments, the amount of component comprising electrolytes is approximately 2% by weight based on the total weight of the dietary composition. In some embodiments, the amount of components comprising electrolytes used in the dietary composition is dependent upon the other components (e.g., ingredients) in the dietary composition (e.g., pectin, thickening agent, and/or water). In some embodiments, the amount of components comprising electrolytes used in the dietary compositions is such that it will maximize prevention and/or treatment of malabsorption dysfunction and/or colonic disorders (e.g., celiac disease, ulcerative colitis, short bowel syndrome), and/or other conditions or disorders, and prevention and/or reduction of a need for parenteral nutrition. In some embodiments, the dissolving of pectin is enhanced in dietary compositions further comprising components comprising electrolytes.

In some embodiments, the dietary compositions comprise water. The dietary compositions are not limited to a particular amount of water. In some embodiments, the amount of water used in the dietary composition is as low as, for example, $1\times10^{-5}$ liters, or as high as $1\times10^8$ liters. In some embodiments, the amount of water may be from approximately 0.1% to 10% by weight based on the total weight of the dietary composition (e.g., 88% to 98% by weight; 90 to 96% by weight; 92% to 94% by weight). In some embodiments, the amount of water is approximately 93% by weight based on the total weight of the dietary composition. In some embodiments, the amount of water used in the dietary composition is dependent upon the other components (e.g., ingredients) in the dietary composition (e.g., pectin, thickening agent, and/or components comprising electrolytes). In some embodiments, the amount of water used in the dietary compositions is such that it will maximize prevention and/or treatment of malabsorption dysfunction and/or colonic disorders (e.g., celiac disease, ulcerative colitis, short bowel syndrome), and/or other conditions or disorders, and prevention and/or reduction of a need for parenteral nutrition. In some embodiments, the water is used to prevent the dietary composition from developing an undesired consistency (e.g., a sticky consistency).

The dietary compositions (e.g., nutraceutical compositions; food products) are not limited to a particular preparation configuration. In some embodiments, the dietary composition comprises approximately 0.1 to 10% by weight thickening agent (e.g., 3% by weight thickening agent) (e.g., gelatin, pudding mix), 0.1 to 10% by weight pectin (e.g., 2.5% by weight pectin), 0.1 to 10% by weight component comprising electrolytes (e.g., CeraLyte 70) (e.g., 2% by weight component comprising electrolytes), and 88% to 98% by weight water (e.g., 93% by weight water). In some embodiments, the dietary composition comprises 7 grams thickening agent (e.g., gelatin, pudding mix), 6 grams pectin, 5 grams component comprising electrolytes (e.g., CeraLyte 70), and 8 ounces water (e.g., approximately 227 grams). In some embodiments, the dietary compositions are prepared for a single serving. In some embodiments, the dietary compositions are prepared in bulk (e.g., 10 servings, 20 servings, 100 servings, 1000 servings 100,000 servings, etc.). The dietary compositions are not limited to a particular form of preparation. In some embodiments, the dietary composition is prepared as, for example, a cake, cookie, bar, lozenge, chewable lozenge, chewable tablet, frozen beverage, unfrozen beverage, a desert, sherbet, soup, cereal, supplement powder, etc. In some embodiments, the dietary compositions are prepared in sealed containers (e.g., sherbet containers).

The dietary compositions (e.g., nutraceutical compositions; food products) are not limited to a particular method for preparation. In some embodiments, the dietary compositions are prepared for human use. In some embodiments, the dietary compositions are prepared for veterinary use. In some embodiments, the method for preparing dietary compositions of the present invention comprise, for example, mixing to a smooth consistency desired amounts of a thickening agent (e.g., gelatin, pudding mix), pectin, a component comprising electrolytes (e.g., CeraLyte 70), and boiling water, and chilling the mixture until firm. In some embodiments, methods for preparing dietary compositions are conducted in a sterile manner such that the dietary composition is suitable for consumption (e.g., oral, parenteral). In some embodiments, the dietary compositions are prepared as a ready-made product. In some embodiments, the dietary compositions are prepared as a ready to make mixture (e.g., a mixture that can be prepared at home). The dietary compositions are not limited to a particular type of ready to make mixture. In some embodiments, the ready to make mixture is, for example, in powder form, dried form, freeze-dried form, and lypholized form. In some embodiments, preparation of the ready to make mixture requires reconstitution.

In some embodiments, the dietary compositions are prepared for room temperature storage conditions (e.g., long term room temperature storage; short term room temperature storage). In some embodiments, the dietary compositions are prepared for freezing storage conditions (e.g., long term freezing temperature storage; short term freezing temperature storage). In some embodiments, the dietary compositions are prepared for refrigerated storage conditions e.g., long term refrigerated temperature storage; short term refrigerated temperature storage).

The dietary compositions (e.g., nutraceutical compositions, food products, food supplements) of the present invention are not limited to a particular method for preventing and/or treating malabsorption dysfunction and/or disorders. In some embodiments, the dietary compositions prevent and/or treat malabsorption dysfunction and/or disorders through, for example, increasing intestinal transit time, decreasing gastric emptying, maintaining fluid balance, increasing energy absorption, and/or increasing fluid absorption. The dietary compositions are not limited to preventing and/or treating a particular malabsorption disorder (e.g., any disorder associated with altered malabsorption function). In some embodiments, examples of malabsorption disorders include, but are not limited to, celiac disease, and short bowel syndrome.

The dietary compositions (e.g., nutraceutical compositions, food products, food supplements) of the present invention are not limited to a particular method for preventing and/or treating colonic disorders. In some embodiments, the dietary compositions prevent and/or treat colonic disorders through, for example, providing short chain fatty acids for the purpose of healing ulcerations and mucosal injury. The methods are not limited to treating a particular kind of colonic disorder and/or associated symptom. In some embodiments, the colonic disorder is ulcerative colitis. In some embodiments, the colonic disorder includes, but is not limited to, angiodysplasia of the colon, chronic functional abdominal pain, colitis, colon cancer, constipation, Crohn's disease, diarrhea, diverticulitis, diverticulosis, irritable bowel syndrome, polyposis (e.g., colorectal polyp), ulcerative colitis, and toxic megacolon. In some embodiments, the symptoms associated with a colonic disorder include, but are not limited to, at least one of inflammation of the lining of the colon, ulcers, bleeding, diarrhea (e.g., diarrhea mixed with blood and mucus), abdominal pain, and weight loss.

In some embodiments, the dietary compositions (e.g., nutraceutical compositions, food products, food supplements) are co-administered and/or co-prepared with additional agents. The dietary compositions are not limited to a particular type of additional agent. In some embodiments, the additional agents are designed to prevent and/or treat malabsorption dysfunction (e.g., antibiotics (e.g., gentamycin), bile acid-binding agents (e.g., cholestyramine), digestive enzymes (e.g., pancrelipase)). In some embodiments, the additional agents are designed to prevent and/or treat colonic disorders (e.g., ulcerative colitis) and associated symptoms (e.g., 5-Aminosalicyclic acid agents (e.g., sulfasalazine, mesalamine, balsalazide), tumor necrosis factor inhibitors (e.g., infliximab), immunosuppressants (e.g., azathioprine, cyclosporine, 6-mercaptopurine), antimicrobials (e.g., ciprofloxacin, metronidazole), corticosteroids (e.g., methylprednisolone, prednisone)). In some embodiments, the additional agents are health supplements (e.g., vitamins, energy boosting agents, etc.). In some embodiments, the additional agent is a sweetening agent (e.g., sugar, artificial sugar, a flavoring agent, etc.).

EXAMPLE

The present invention may be better understood by reference to the following non-limiting Example. The following example is presented in order to more fully illustrate certain embodiments of the invention. The present invention is not restricted to the following Example, and it is understood by one skilled in the art that many variations are possible within the spirit and scope of the present invention.

Pectin is water soluble, non-cellulose fiber that is nearly completely fermented by bacterial colonic flora to short chain fatty acids (SCFA). In animal models, SCFA promote colonic water absorption and small bowel nitrogen absorption. It was contemplated that pectin supplementation enhances fluid and macronutrient absorption by prolonging oro-cecal transit time and by enhancing colonic fluid absorption.

Six human subjects (3 males and 3 females) aged 29-67 years old with short bowel syndrome were studied, all with jejunal-colonic anastomosis, and 4 of which required long-term parental nutrition (PN). Mean residual small bowel length was 50.3±36.5 cm and mean residual colon length was 39.3±5.09 cm. The 4 patients requiring PN had received it for 4.75 years (SD: 3.86). At the time of the study, they received 9.93±9.75 kcal/kg/d with infusion 4±2.45 days/wk. Subjects were admitted for 2 visits each lasting 6 days, separated by 2 weeks. During their initial visit, 25 g D-xylose test, indirect calorimetry, radioisotope gastric emptying study and SmartPill© (Buffalo, N.Y.) tests were performed. Macronutrient balance studies were performed: all stool and urine were collected for 3 days (days 3-5), weighed, and an aliquot of the pooled samples analyzed for SCFA, nitrogen, carbohydrate, fat, and energy measurements. Self-selected standardized meals were provided in duplicate, and equivalent portions consumed by the subjects were weighed and analyzed for nitrogen, fat, carbohydrate, and energy. Following completion of stool and urine collection, a custom pectin-based oral supplement (GENU® pectin type B rapid set-Z, CP Kelco, Copenhagen, Demark), that provided 6 g of citrus pectin prescribed tid in addition to usual meals. Subjects continued the pectin supplement at home and were readmitted after 2 weeks when all tests were repeated in the same format as the first visit. A delay in the emptying of the stomach and a slowing of intestinal transit time was observed. Pectin supplementation resulted in increased SCFA production.

All publications and patents mentioned in the above specification are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A dietary composition comprising 2-4% by weight pectin, 2-5% by weight thickening agent, 0.5-4% by weight electrolyte component, and water, wherein the dietary composition is a pudding.

2. The dietary composition of claim 1, wherein said dietary composition is prepared as a nutraceutical composition, a food product, or a prebiotic food supplement.

3. The dietary composition of claim 1, wherein said dietary composition is prepared for oral consumption by a human subject.

4. The dietary composition of claim 1, wherein said dietary composition is configured to treat malabsorption dysfunction and/or a colonic disorder in a subject.

5. The dietary composition of claim 1, wherein said dietary composition increases intestinal transit time in said subject.

6. The dietary composition of claim 1, wherein said dietary composition decreases gastric emptying.

7. The dietary composition of claim 1, wherein said dietary composition increases intestinal energy absorption and/or increases intestinal fluid absorption.

8. The dietary composition of claim 1, wherein said dietary composition treats colonic ulcerations and/or colonic mucosal injury.

9. The dietary composition of claim 1, wherein said electrolyte component is 70 mEq sodium, 20 mEq potassium, 60 mEq chloride and 30 mEq citrate.

10. The dietary composition of claim 1, wherein said thickening agent is gelatin.

11. The dietary composition of claim 1, wherein said thickening agent is pudding mix.

12. The dietary composition of claim 1, wherein said dietary composition further comprises a sweetening agent.

13. A method for treating a subject, comprising administering the composition of claim 1 to a subject.

14. The method of claim 13, wherein the subject is human.

15. The method of claim 13, wherein the subject has a malabsorption dysfunction.

16. The method of claim 15, wherein the malabsorption dysfunction is selected from the group consisting of Crohn's disease and short bowel syndrome.

17. The method of claim 13, wherein the subject has a colonic disorder.

18. The method of claim 16, wherein said colonic disorder is ulcerative colitis.

19. A method of manufacturing the dietary composition of claim 1, comprising mixing pectin, thickening agent, and an electrolyte component with boiling water, and cooling said mixture.

20. The method of claim 19, wherein said cooled mixture consists of approximately 3% by weight thickening agent, 2.5% by weight pectin, 2% by weight electrolyte component, and 92.5% by weight water.

* * * * *